(12) United States Patent  (10) Patent No.: US 7,812,945 B2
Fortier et al.  (45) Date of Patent: Oct. 12, 2010

(54) FLUORESCENCE TOMOGRAPHY USING LINE-BY-LINE FORWARD MODEL

(75) Inventors: Simon Fortier, Montreal (CA); Frederic Leblond, Montreal (CA)

(73) Assignee: Art Advanced Research Technologies Inc., St-Laurent, QC (CA)

( * ) Notice: Subject to any disclaimer, the term of this patent is extended or adjusted under 35 U.S.C. 154(b) by 514 days.

(21) Appl. No.: 11/764,041

(22) Filed: Jun. 15, 2007

(65) Prior Publication Data

US 2008/0312879 A1    Dec. 18, 2008

(51) Int. Cl.
G01J 3/30    (2006.01)
(52) U.S. Cl. ........................ 356/317; 600/317
(58) Field of Classification Search .................. 356/317; 600/317
See application file for complete search history.

(56) References Cited

U.S. PATENT DOCUMENTS

| | | | |
|---|---|---|---|
| 5,865,754 A * | 2/1999 | Sevick-Muraca et al. .... | 356/317 |
| 6,825,928 B2 * | 11/2004 | Liu et al. ..................... | 356/317 |
| 2004/0015062 A1 * | 1/2004 | Ntziachristos et al. ....... | 600/312 |
| 2008/0146897 A1 * | 6/2008 | Alfano et al. ............... | 600/310 |

* cited by examiner

*Primary Examiner*—Kara E Geisel
(74) *Attorney, Agent, or Firm*—BCF LLP

(57) ABSTRACT

A fluorescence optical tomography system and method uses a photon migration model calculator for which absorption and reduced scattering coefficient values are determined for each source/detector pair. The coefficient values may be determined by measurement, in which a time resolved detector detects the excitation wavelength and generates temporal point spread functions from which the coefficient values are found. Alternatively, the coefficient values may be determined by calculating them from a dataset containing a spatial distribution of absorption and reduced scattering coefficients in a volume of interest. The fluorescence detection may be continuous wave, time resolved, or a combination of the two. An estimator uses a detected fluorescence signal and an estimated fluorescence signal to estimate the image values.

23 Claims, 5 Drawing Sheets

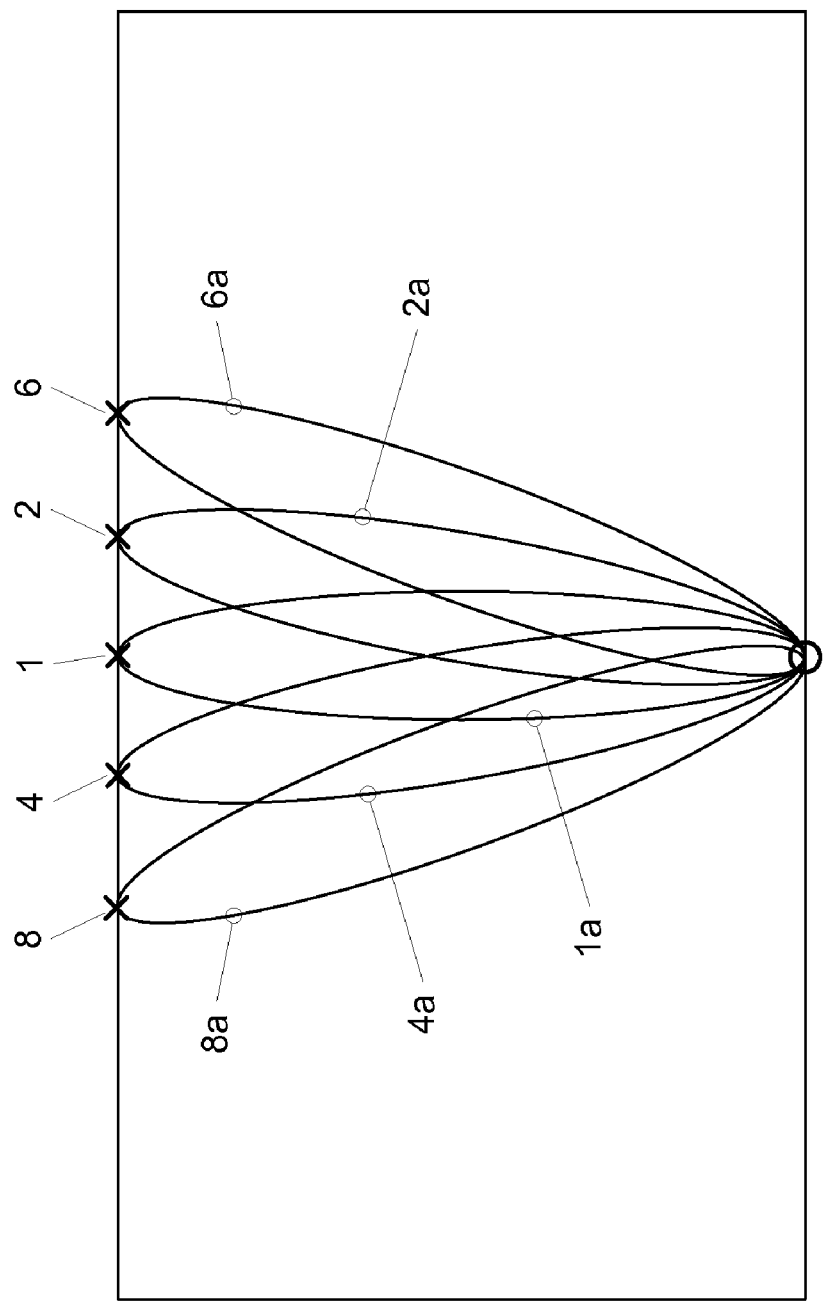
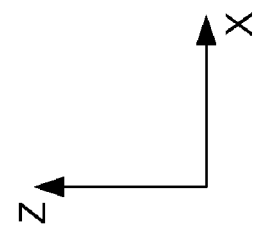

FLUORESCENCE TOMOGRAPHY USING LINE-BY-LINE FORWARD MODEL

FIELD OF THE INVENTION

This invention relates generally to the field of fluorescence optical imaging of turbid media.

BACKGROUND OF THE INVENTION

Imaging of mammalian tissues has been used extensively to obtain information on the internal structures as well as on the biodistribution of molecules. This information can of course be utilized for diagnosis purposes. Several techniques based on different physical principles are currently available to obtain images that encompass a broad range of spatio-temporal resolution. Such techniques include Magnetic Resonance Imaging (MRI), Positron Emission Tomography (PET), single-photon emission computed tomography (SPECT), X-ray, ultrasound and, now emerging, optical imaging.

In optical imaging, three approaches have been used to generate the optical data necessary to reconstruct images of volume of interest (VOI). The continuous wave (CW) technique uses a continuous wave light source and allows the measurement of light attenuation. The time domain (TD) technique involves injecting a pulse of light of short duration into the VOI and detecting the light as a function of time as it exits the VOI. Finally, the frequency domain (FD) technique relies on frequency modulation of a light source and analysis of the phase and amplitude of the resulting optical signal as it exits the VOI. Together, time domain and frequency domain may be referred to as "time-resolved" (TR).

Characterization of the VOI in optical imaging relies on a determination of the absorption and scattering characteristics of the different regions of the VOI. Starting with assumptions for absorption and scattering values, measurements are then taken and used to modify these assumptions to improve the image data. Light that is injected into the VOI at one point is detected as it exits at another point, and the detected signal provides information regarding the region through which the light passed. Attenuation of the light transmitted through the VOI due to absorption and scattering is quantifiable at the detector. Moreover, the TD technique allows the generation of a time point spread function (TPSF), which provides additional information regarding the extent to which the attenuation is due to absorption or due to scattering. This allows the decoupling of the two primary detected optical parameters of interest, the absorption coefficient $\mu_a$ and the reduced scattering coefficient $\mu_s'$. By sampling the VOI using a number of different source and detector positions, more detailed spatial information regarding the structure of the VOI is obtained, allowing a three-dimensional image to be constructed.

Fluorescence diffuse optical tomography (FDOT) systems obtain three-dimensional images showing the location and number density of fluorescent molecules embedded in a biological medium. Typically, this is achieved using a large set of surface measurements combined to a photon propagation model. For highly scattering media, ($\mu_s' > 10\mu_a$), photon propagation is well approximated by solutions to the diffusion equation. A further simplification that is often made consists in using analytical solutions to the diffusion equation for forward model building. In this case, an assumption is made that the absorption and scattering properties of the medium are constant throughout. This approximation is convenient when considering commercial devices because it allows fluorescence image reconstructions to be performed in a relatively short processing time. For in vivo imaging however, the optical property heterogeneities associated with the non-trivial anatomy of the animal cannot simply be neglected. To that effect, more sophisticated (and time-consuming) methods exist where photon propagation is actually computed using the a priori information related to organs and tissues (spatial distribution and optical properties). Aside from the use of a priori structural information, proposals have been made in the past to help minimize the impact of optical heterogeneities on fluorescence data. For example, the Born normalization scheme for tomography data sets has been experimentally shown to significantly improve the quality of reconstructed fluorescence images.

For a heterogeneous sample, such as a small animal, the variations in composition of the sample from one location to another complicate the problem of acquiring an accurate image of the VOI. In the absence of a priori structural and anatomical information obtained through another modality such as microCT, PET, SPECT or MRI systems, conventional FDOT systems typically make the assumption of constant absorption and scattering properties throughout the medium, as mentioned above. However, such an assumption is crude, and is particularly ineffective when performing imaging in vivo, and the alternative of using information gathered from another modality may be unattractive as it significantly complicates the imaging process.

SUMMARY OF THE INVENTION

In accordance with the present invention, a fluorescence optical tomography method and system are provided that use values for absorption and reduced scattering coefficients $\mu_a$ and $\mu_s'$ determined for each source/detector pair to improve the calculation using the photon migration model without significantly increasing the computational burden relative to the use of global estimates for $\mu_a$ and $\mu_s'$. The tomography system produces an image of a volume of interest indicative of location and number density of fluorophores embedded therein, and relies on optical scanning of the volume at a plurality of source/detector geometries. An optical source, which may include multiple discrete sources, generates an optical signal at an excitation wavelength that interacts with the fluorophores to cause fluorescence therefrom at a fluorescence wavelength. A time resolved detector may be used to detect the excitation wavelength and provide an input to a determinator that determines separately, for each of the source/detector geometries, an absorption coefficient and a reduced scattering coefficient. Alternatively, predetermined information about the spatial distribution of optical properties in the sample of interest (coming from such means as optical imaging or multimodal imaging) may be provided as an input to a determinator that determines separately, for each of the source/detector geometries, an effective absorption coefficient and an effective reduced scattering coefficient. A photon migration model calculator receives the absorption and reduced scattering coefficients and uses them in calculating a forward model which gives the approximate relative contribution of each voxel within the volume of interest to the fluorescence signal.

The fluorescence wavelengths are detected by a detector that generates a fluorescence signal output. This output is directed to an estimator which uses it together with a calculated fluorescence signal from the photon migration model calculator to adjust the estimated spatial distribution of fluorophore concentration and generate an image. This may be an exact inverse solving, in which the estimation is done one time, or it may be done iteratively to reduce mismatch between the experimental data and the simulated data. If done iteratively, the image data may then be directed to the photon migration model calculator to generate a revised approximated fluorophore concentration. The estimator uses it together with the fluorescence signal to update the image data. This process of generating revised image data, recalculating and updating the image may continue until image errors are satisfactorily reduced.

The present invention improves over the prior art method of using global estimates for the absorption and reduced scattering coefficients, and is referred to as a "line-by-line" method whereby the photon migration model calculator uses a matrix, i.e., forward model, for which each line (representing a different source/detector geometry) receives different optical properties as inputs. Detection of the fluorescence wavelengths may use different methods, as appropriate. In one embodiment, a continuous wave source is used, and the fluorescence wavelengths are detected with a continuous wave detector. The output of this detector is then supplied to the estimator, along with the output from the photon migration model calculator, which is a continuous wave photon migration model calculator. In another embodiment, a pulsed laser source is used, and the fluorescence wavelengths are detected using a time resolved detector. A temporal point spread function is generated for the fluorescence wavelengths, which is then compiled with a TPSF compiler before being provided to the estimator. In this embodiment, the photon migration model calculator is a time resolved photon migration model calculator.

BRIEF DESCRIPTION OF THE DRAWINGS

FIG. 2 is a schematic, cross-sectional view of the volume of FIG. 1 showing a variety of possible source/detector geometries and the resulting main area of photon migration, predicted by a model of assuming homogeneous optical properties.

DETAILED DESCRIPTION

Figure 1:
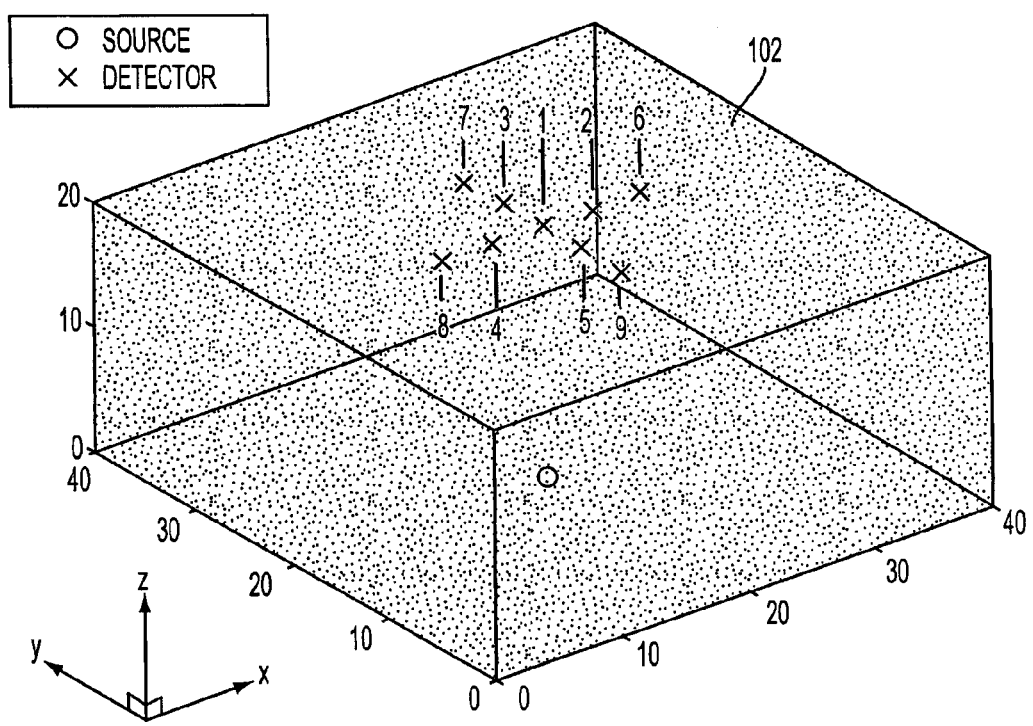
FIG. 1 is a schematic view of a sample volume that might be imaged using the present invention.

Shown in FIG. 1 is a schematic image of a sample 102 comprising a volume of interest (VOI) which might be selected for examination using the present invention. For ease of description, the VOI shown in the figure has the shape of a right angle parallelepiped, but those skilled in the art will recognize that the actual shape may be different. In this example, the volume is to be scanned using one source location (indicated by a "O" in the figure) and nine detector locations (each indicated by an "X") in the figure. As shown, the detectors are arranged in a "cross-shape" geometry, and the detectors and the source are positioned, respectively, on opposite sides of the sample. Relative to the Cartesian coordinate system shown in the figure, tomographic data is collected by raster-scanning this configuration over a two-dimensional region of interest in the x-y plane.

The construction of an optical fluorescence model using the present invention does not use values for absorption and reduced scattering that are constant throughout the medium. Rather, the model uses information collected regarding the optical properties $\mu_a$ and $\mu_s'$ of the medium for each of the source/detector pairs used in the imaging process. That is, instead of global optical properties that are constant throughout the medium, the present invention uses measured local effective properties that are specific to each source/detector combination. In the case of a VOI like that shown in FIG. 1, there would be multiple different sets of local effective optical properties, $\mu_a$ and $\mu_s'$, the total number of sets being equal to nine (for the total number of detectors) times the number of source positions included in the scan.

FIG. 2 depicts a schematic view of one vertical plane of the volume shown in FIG. 1, as indicated by the X-Z coordinate designation in the figure, which corresponds to the three-dimensional coordinate system of FIG. 1. The plane shown in FIG. 2 is a plane which passes through a center point of the "cross-shape" geometry of the detector arrangement, that is, it is the plane along which each of the detectors designated as 1, 2, 4, 6 and 8 are aligned, along with the source. For each detector 1, 2, 4, 6, 8, FIG. 2 also shows an area (labeled, respectively, 1a, 2a, 4a, 6a and 8a) within the plane that represents a cross section of the photon migration volume between the source and the detector in question. This volume represents the space through which photons emitted by the source may propagate and have an acceptable likelihood of being detected by the detector in question. That is, photons exiting this volume have an extremely low probability of being detected at the detector in question, and regions outside of the volume do not contribute sufficiently to a signal detected by the detector in question to provide information regarding the medium. Thus, a detected signal for a given source/detector pair provides information regarding mostly the designated volume between the source and detector. Those skilled in the art will recognize that although FIG. 2 shows just a two-dimensional schematic representation of the photon migration volume for each detector, the actual volume is roughly rotationally symmetric about a straight line between the center of each of the source and detector. Furthermore, it will be apparent that, while the example of FIGS. 1 and 2 show a single source with multiple detectors, multiple sources with multiple detectors may also be used.

The model expression for time-resolved data collected at the detector is given by the convolution of three functions: (1) the propagator from the isotropic source to a fluorescent molecule inside the medium; (2) the quantum mechanical excitation and de-excitation of the fluorophore, and (3) the photon transport to the collection point. The Fourier components of this expression, including potential contributions from all infinitesimal volume elements, are $$\Phi^E(\vec{r}_s, \vec{r}_d, \omega) = \frac{N_0}{\sqrt{2\pi}} \int d^3 r_f \Theta_d(\vec{r}_d) G^E(\vec{r}_f, \vec{r}_d, \omega) \frac{\varphi \varepsilon C_T(\vec{r}_f)}{1 - i\omega\tau} \Theta_s(\vec{r}_s) G^X(\vec{r}_s, \vec{r}_f, \omega) \qquad (1)$$

where the labels s, d, f respectively stand for source, detection and fluorophore locations while $G^E$ and $G^X$ represent the frequency domain Green functions of the diffusion equation at the fluorophore emission and excitation wavelengths, respectively. Included in the equation are the source and detector experimental coupling constants, respectively, $\Theta_s$ and $\Theta_d$. These parameters are essential because they contain, in principle, all information related to inconsistencies with the model due to systematic experimental errors. For example, these would include optical effects caused by defects on the surface of the animal that could not be accounted for in the scope of the diffuse optical model. In reality, the coupling factors cannot be determined directly for all source and detector pairs involved in a tomography algorithm. Therefore, the normalized field is considered, being represented as follows:

$$\Phi^N(\vec{r}_s, \vec{r}_d, \omega) = \frac{1}{\sqrt{2\pi}} \frac{\Phi^E(\vec{r}_s, \vec{r}_d, \omega)}{\Phi^X(\vec{r}_s, \vec{r}_d, \omega)} \quad (2)$$

where $\Phi^X$ is the fluence collected at the fluorophore excitation wavelength. Experimentally, this field must be acquired separately from fluorescence data. Since the spatial locations of the source and detectors for both scans are identical, it may readily be seen that the coupling factors are cancelled in $\Phi^N$ (when neglecting variations of detector spectral response between the excitation and fluorescence wavelengths). Roughly, the latter may be regarded as the Fourier components of the time-dependent fluorescent field from which diffusive effects have been removed, although this is not exactly true in that the paths (on average) followed by photons associated with the scans $\Phi^E$ and $\Phi^X$ are only approximately the same. However, using the Born normalization scheme can significantly reduce the impact of optical properties heterogeneities when homogeneous propagators are used.

The present invention uses a method for improving the potential of the forward model to match fluorescence data. Those skilled in the art will recognize that combining this method with the use of Born normalized data may improve even further the quality of reconstructed fluorescence images. In the scope of a tomography algorithm, expression (1) above needs to be computed repeatedly for all source-detector combinations. In a conventional system, global optical property estimates are used, i.e., the same values of $\mu_a$ and $\mu_s'$ are considered whenever (1) is evaluated. But, in accordance with the present invention, those global estimates are replaced by local effective optical properties, $\mu_a^{\text{Eff}}$ and $\mu_s'^{\text{Eff}}$, for every combination of $\vec{r}_s$ and $\vec{r}_d$ when computing equation (1) or (2). This method may be referred to as a "line-by-line" approach, since each source-detector pair in the forward model is represented by a matrix line.

The method of the present invention has the advantage of maintaining the complexity of the original model while taking advantage of a priori information related to the optical properties of the sample. The evaluation of these effective optical properties depends on the type of a priori information available. For example, when time-domain data is available at the excitation wavelength, $\mu_a^{\text{Eff}}$ and $\mu_s'^{\text{Eff}}$ may be obtained by least-squares fitting of the time-dependent solution to the diffusion equation onto the excitation data. Alternatively, when volumetric information about the optical properties of the sample is available (e.g., from MRI, CT or even 3D endogenous optical images), the following steps may be used to estimate $\mu^{\text{Eff}}$ (which refers to either $\mu_a^{\text{Eff}}$ or $\mu_s'^{\text{Eff}}$) for each source-detector combination.

The value $\mu(\vec{\rho})$ is assumed to be the value of the absorption (or reduced scattering) coefficient for all locations $\vec{\rho}$ in the biological sample targeted for reconstruction. To obtain an estimate of $\mu^{\text{Eff}}$ for each source-detector pair, a weighted average $\mu(\vec{\rho})$ is considered, $$\mu^{\text{Eff}}(\vec{r}_s, \vec{r}_d) = \frac{\int_\rho W(\vec{r}_s, \vec{r}_d, \vec{\rho}) \mu(\vec{\rho}) \delta\rho}{\int_\rho W(\vec{r}_s, \vec{r}_d, \vec{\rho}) \delta\rho} \quad (3)$$

where W is a spatially-dependent weight function. The choice for this function takes into account the physical phenomena involved in a simple product of two analytical homogeneous Green's functions evaluated at the excitation wavelength. One possibility might be the following:

$$W(\vec{r}_s, \vec{r}_d, \vec{\rho}) = G^X(\vec{r}_s, \vec{\rho}) \times G^X(\vec{\rho}, \vec{r}_d) \quad (4)$$

In addition, the invention further includes the possibility of performing this as an iterative process. Thus, upon having computed $\mu_a^{\text{Eff}}$ and $\mu_s'^{\text{Eff}}$ for each source-detector pair and using the obtained values in equation (1), a better estimate of W has been made available. This estimate may therefore be used in turn as a more precise weight function in equation (3). As will be apparent to the person skilled in the art, this process may be repeated as many times as desired to further refine the estimate.

Figure 3:
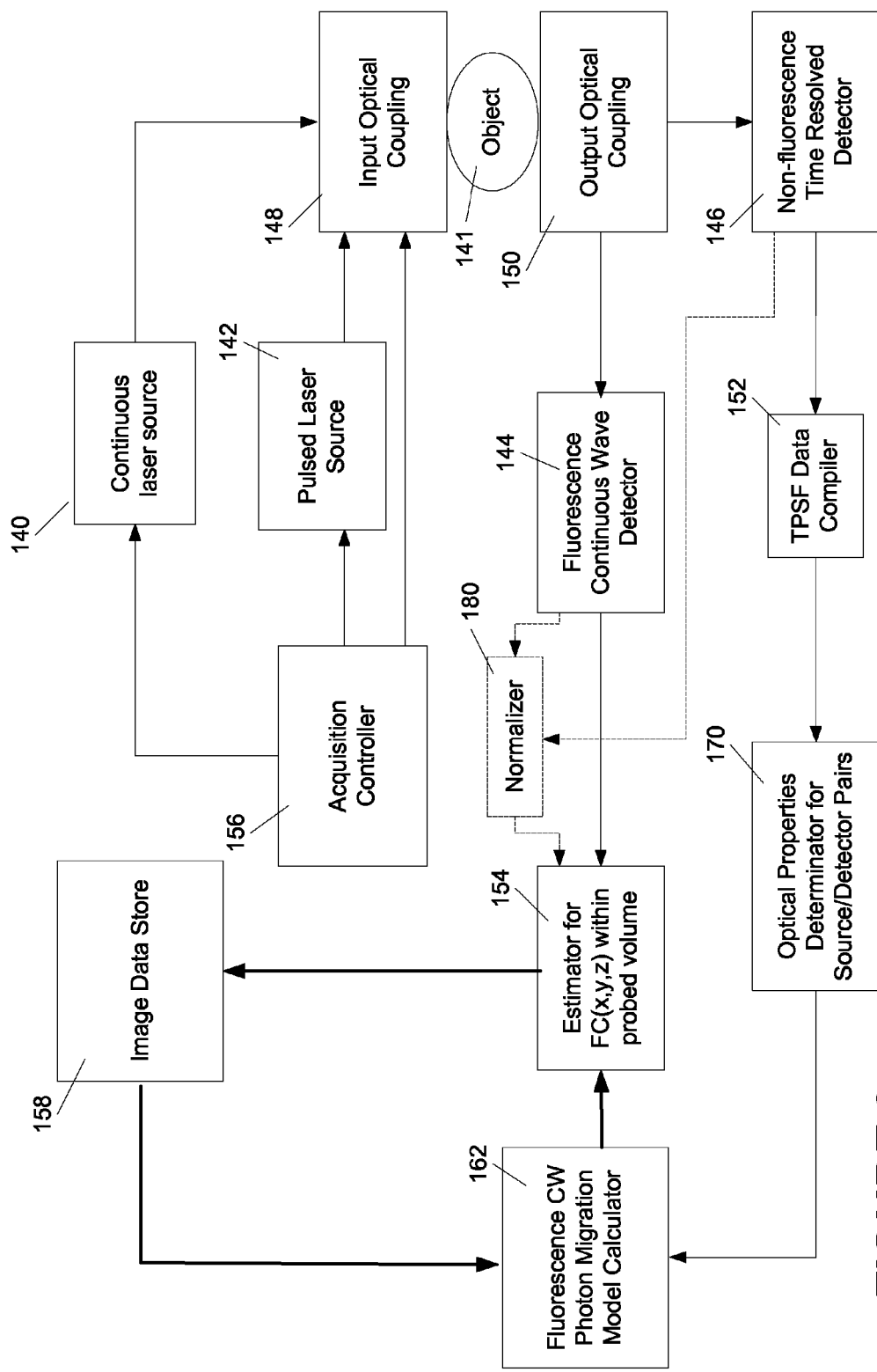
FIG. 3 is a block diagram of an embodiment of the present invention that uses continuous wave detection of fluorescence wavelengths.

FIG. 3 shows a block diagram of a first embodiment of a system according to the present invention. Those skilled in the art will understand that this is but an exemplary embodiment of the invention, and variations may exist. A continuous laser source 140 and a pulsed laser source 142 are provided to inject light into a sample object, such as that shown in FIG. 1. As shown in FIG. 3, input optical coupling 148 is provided to guide the light from the two sources into the object 141. In this embodiment, the optical coupling is common to the two optical sources, but alternative arrangements are also possible. Light exiting the sample is collected using output optical coupling 150 that is, in turn, coupled to a continuous wave detector 144 and a time-resolved detector 146. A time-resolved (photon counting) detector might also be used to collect both the time resolved signal and the continuous wave signal. As with the input optical coupling, the output optical coupling may take different forms as desired for the specific application. Both, for example, may be realized using known technologies such as optical fibers, free-space optics and the like.

In the embodiment of FIG. 3, the fluorescence data is collected only in the continuous wave mode, while data regarding the characterization of the medium, as represented by the absorption and scattering characteristics thereof, is collected only at the excitation wavelengths from pulsed laser source 142 in the time domain. As discussed below, it may also be desirable to perform time-resolved detection for collecting fluorescence data. However, the continuous wave acquisition scheme has the advantage of shorter acquisition time and, for fluorescence signal detection, a continuous wave laser source is significantly less expensive than the time domain acquisition scheme.

Acquisition controller 156 oversees the operation and coordination of the laser sources, including the selection of the source position via an output signal to coupling device 148. In an arrangement such as that shown in FIG. 1, there is only a single source position used, but other embodiments may make use of multiple source positions. This may be achieved by way of an optical switch, or sub-assembly with motors allowing the source to be scanned over the sample, in the case of a fiber optic coupling, and in the case of free-space optics by way of a galvo-mirror inserted within the optical system, or sub-assembly with motors allowing the source to be scanned over the sample. The detector coupling device 150 in this embodiment requires no switching control. Rather, the detector has a channel for each detector position, each of which is monitored as appropriate. However, when using free-space optics, the detector position may be controlled by a galvo-mirror or other means to achieve movement of the detection spot over the object.

The time-resolved detector 146 collects data at the excitation wavelength, and is linked to a raw temporal point spread function (TPSF) data compiler 152 that can generate TPSFs. The TPSF data acquired and enhanced may be the full TPSF, a TPSF characteristic parameter, or a plurality of time-gate TPSF points. The output from the TPSF data compiler is fed to an optical properties determinator 170, which determines the values of absorption coefficient $\mu_a$ and reduced scattering coefficient $\mu_s'$ for each source/detector pair. This source/detector specific information is then input to photon migration model calculator 162, which calculates modeled values for fluorophore CW fluence through the medium assuming a spatial distribution of fluorophore concentration FC(x,y,z) according to the current estimate as stored in store 158. Without prior information for fluorophore location, the initial estimate of fluorophore concentration is zero everywhere although, with more prior information, a different initial estimate might be used. From this point, the inverse problem solver begins to build an image. In a conventional system, the model calculation would be performed using a global estimate for each of $\mu_a$ and $\mu_s'$, that is, $\mu_a$ and $\mu_s'$ values that are the same for all source/detector pairs. However, in the present invention, by using detected values that are specific to each source/detector pair, a higher degree of accuracy in the model calculation is produced, without significantly increasing the computational cost.

In a variation of the embodiment of FIG. 3, Born normalization may be used with the system. The general principles of Born normalization are known in the art, and are not repeated in any significant detail herein. Such normalization is not required, but may be a desirable option in that it dampens the impact of heterogeneities without the need to compute a complex, fully-heterogeneous forward model. If normalization is used in the embodiment of FIG. 3, the output from continuous wave detector 144, before being input to estimator 154, undergoes normalization by normalizer 180. This normalization of the detected signal is with regard to measurements of the medium and, therefore, detected excitation data is supplied to the normalizer 180 via an input from non-fluorescence time resolved detector 146. Those skilled in the art will recognize that, if the detected data is normalized, the photon migration model calculator 162 will also use normalized model data. The normalizer 180 and its related connections are shown in broken lines in the figure to indicate that it is not mandatory and that its use represents a variation on the embodiment of FIG. 3.

The fluorescence optical signal is detected by continuous wave detector 144, which then provides an output to estimator 154. The estimator 154 receives this input, and the input from the photon migration model calculator, and adjusts the estimate of the spatial distribution of fluorescence concentration. The estimates are as a function of space within the volume, and are therefore represented by the "fluorophore concentration" function FC(x,y,z). Using the collected data and the inputs from the photon migration model calculator 162, the estimator 154 makes estimates of fluorophore concentration at each location in the x,y,z coordinate system of the volume of interest. These estimates are stored in image data store 158. If there is an exact inverse solving, the output of the estimator is simply stored in the image data store 158. If the estimation process is to be continued, the updated image data is then made available to the photon migration model calculator which uses it to provide updated values of fluorophore concentration to the estimator in the next iteration. This iterative process may thereafter continue until the errors (i.e., residual representing the mismatch between model predictions and data) are reduced to an acceptable level.

Figure 4:
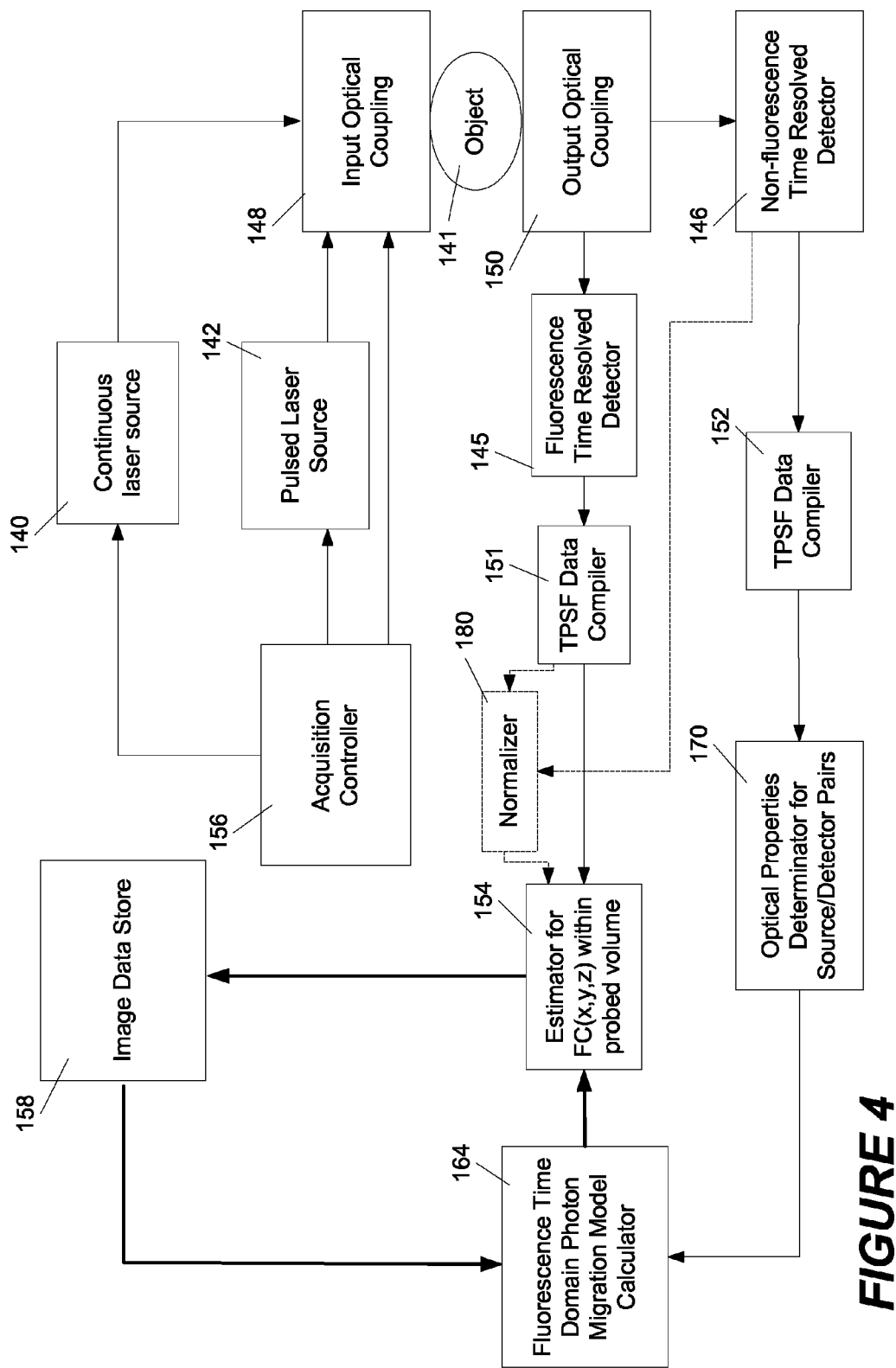
FIG. 4 is a block diagram of an embodiment of the present invention that uses time resolved detection of fluorescence wavelengths.
Figure 5:
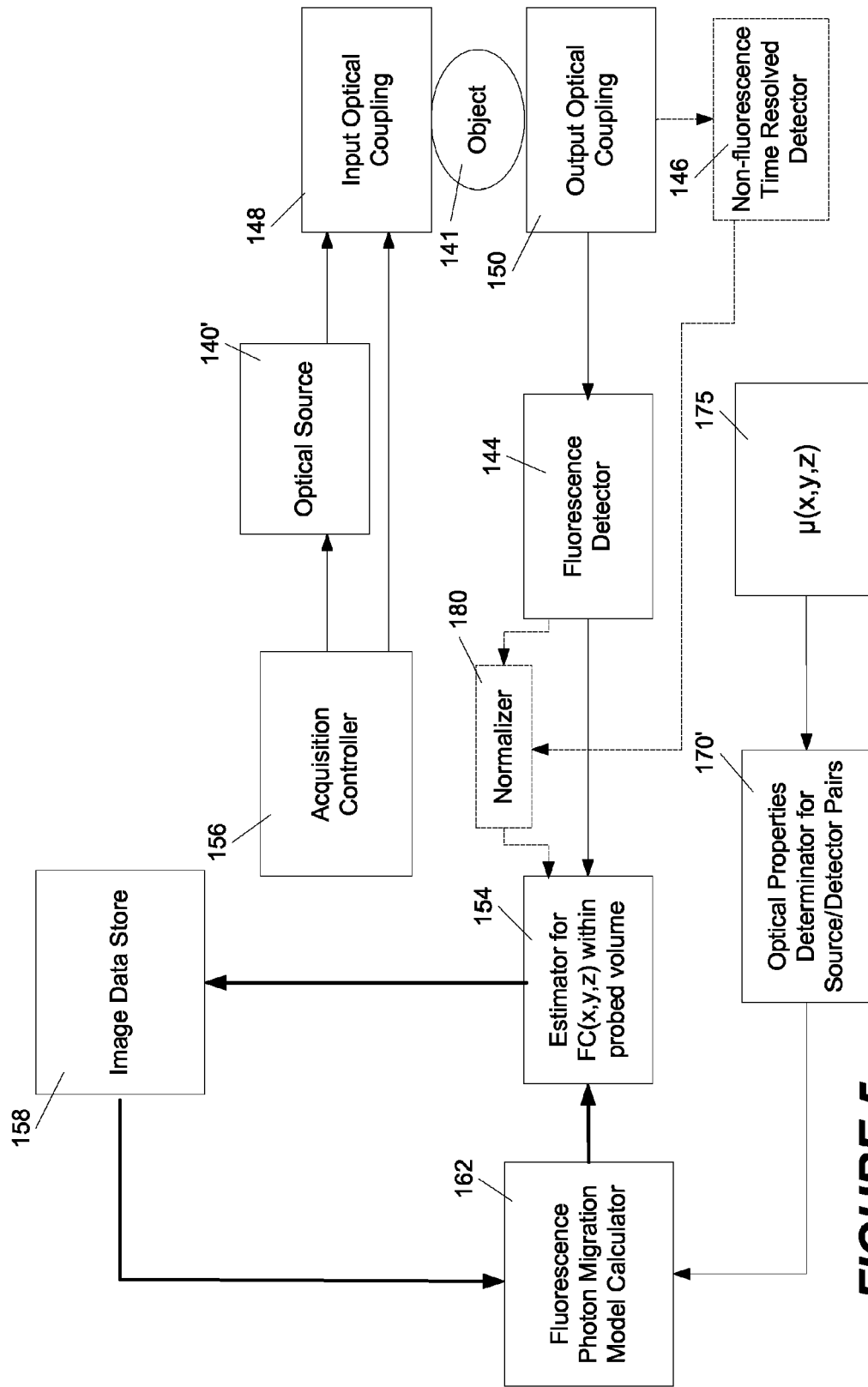
FIG. 5 is a block diagram of an embodiment of the present invention that uses calculated values for the effective absorption and reduced scatter coefficients for the medium as seen between each source and detector position in the forward fluorescence photon migration model calculator.

In the diagrams of FIGS. 3 to 5, it is important to note that the photon migration model calculators 162 and/or 164 operate for each desired source-detector pair, and the specific control over the calculators involving the specification of the source-detector geometry is not illustrated for simplicity of illustration. The optical property data from module 170 or 170' is a dataset of optical property values for the desired source-detector geometries that is made available to the model calculators. The specification of the desired source-detector geometries can be predetermined, or determined by an operator, in the latter case, controller 156 can establish a dataset of the geometries and make it available to the modules requiring the dataset. The estimator 154 may also maintain a store of the measured optical values, namely the CW or time-resolved datasets, for all source-detector geometries. Modules 162, 164, 158 and 154 are essentially provided in software on a computer along with their required dataset stores. In some embodiments, this same computer is also used for providing in software modules 156, 151, 152 and 170 or 170'. As will be appreciated by those skilled in the art, the remaining modules are essentially made of known hardware devices.

Shown in FIG. 4 is a block diagram of an embodiment similar to that of FIG. 3, but in which the detection of fluorescence wavelengths is done using a time resolved detector, namely a time domain system. In this embodiment, the acquisition controller 156 controls the pulsed laser source 142 and the input optical coupling 148 so as to provide appropriate injection of light into the object 141 for performing non-fluorescence time resolved detection, as in the embodiment of FIG. 3, and also for fluorescence time resolved detection. Thus, the figure shows a non-fluorescence time resolved detector 146 and a fluorescence time resolved detector 145 for collecting time resolved data of the fluorescence signal from the fluorophores in the volume of interest.

It will be appreciated that when the time-resolved system is frequency domain, the pulsed light source 142 is replaced by a modulated light source, and the time-resolved detector 145 and 146 is replaced by instrumentation able to measure amplitude and phase of the modulated light appearing at the detector. An equivalent to TPSF data compiler 151 or 152 is generally not required when conducting frequency domain measurements.

As shown in FIG. 4, the fluorescence time resolved detector 145 receives an input from the output optical coupling 150 and provides an output to TPSF data compiler 151. The TPSF data compiler 151 generates TPSF data that is output to the estimator 154. As in the embodiment of FIG. 3, the non-fluorescence time resolved detector provides an output to the TPSF data compiler 152 which, in turn, provides TPSF data to the determinator 170. The determinator 170 uses the TPSF data to determine values for $\mu_a$ and $\mu_s'$ separately for each source/detector pair and provides this information to the photon migration model calculator 164. As shown, for this embodiment the photon migration model calculator is specific to time domain fluorescence data, since that is the nature of the data being collected by detector 145. It is possible, however, to also use a continuous wave photon migration model calculator if the data being collected with the time resolved detector is limited to continuous wave data.

In FIG. 4, the estimator receives inputs from the photon migration model calculator 164 and the TPSF data compiler 151 and, using this data, makes estimates of fluorophore concentration in the volume of interest, which are stored in image data store 158. If there is an exact inverse solving, the output of the estimator is simply stored in the image data store 158. If the estimation process is to be continued, the updated image data is made available to the photon migration model calculator, which uses it to provide updated values of fluorophore concentration to the estimator. This iterative process may thereafter continue until the errors are reduced to an acceptable level.

It is also an option in this embodiment to make use of Born normalization, as is described above with regard to FIG. 3. To do normalization in the FIG. 4 embodiment, the output from TPSF data compiler 151 is directed to normalizer 180. The normalizer normalizes the data using excitation wavelength data from the non-fluorescence time resolved detector 146. As discussed above with regard to the embodiment of FIG. 3, the photon migration model calculator would use normalized model data when the detected signal was being normalized. In this way, estimator 154 receives normalized data from both the detection side and the model side of the system. Since the use of normalization is not mandatory, and is a variation of the embodiment shown in FIG. 4, the normalizer 180 and its connections are depicted in the figure using broken lines.

In the embodiment of FIG. 5, the values of $\mu_a^{Eff}$ and $\mu_s'^{Eff}$ are not measured from the object 141 directly, but instead they are calculated for each source-detector geometry from a data store 175 containing the full spatial distribution of $\mu(\vec{\rho})$ using equation (3). That is, the optical properties determinator 170', in this embodiment, calculates the values of $\mu_a^{Eff}$ and $\mu_s'^{Eff}$ from the data received from data store 175. $\mu(\vec{\rho})$ may be determined by optical time-resolved imaging of object 141, in which the values of $\mu_a^{Eff}$ and $\mu_s'^{Eff}$ were not retained, and thus are calculated. In other embodiments, module 175 is a processor that contains a store of $\mu(\vec{\rho})$ for a generic object, and then takes another dataset representing the anatomical geometry of the object 141, such as an image of a different modality, and morphs the distribution of $\mu(\vec{\rho})$ accordingly to obtain $\mu(\vec{\rho})$ for the object 141.

Similar to the previous two embodiments, the embodiment of FIG. 5 may make use of the option of Born normalization. Thus, the optional normalizer 180 is shown in the figure and, if normalization is used, the photon migration model 162 uses normalized model values. Non-fluorescence time resolved detector 146 is also shown in the figure, and it provides the detected excitation data to the normalizer 180. However, if there is no normalization used in the FIG. 5 embodiment, neither the normalizer nor non-fluorescence detector is necessary, since the detection of the excitation wavelength is not needed for the determination of the source/detector specific optical properties.

It will be apparent to those skilled in the art that the implementation of the invention, as shown and described in the foregoing embodiments, may include software, hardware and firmware components, in addition to discrete devices such as the source and detector. Although the block diagrams of FIGS. 3-5 show the details of the invention, the specific manner of implementation may vary, and such variations are considered to be within the scope of the invention. Moreover, while the invention has been shown and described with reference to a preferred embodiment thereof, it will be appreciated by those skilled in the art that various changes in form and detail may be made herein without departing from the spirit and scope of the invention as defined by the appended claims.

What is claimed is:

1. A fluorescence optical tomography method for producing an image of a volume of interest indicative of location and number density of fluorophores embedded therein, the method comprising:
   optically scanning the volume of interest at a plurality of source/detector geometries with an optical source generating an optical signal at an excitation wavelength, interaction of the excitation wavelength with the fluorophores causing fluorescence therefrom at a fluorescence wavelength;
   determining separately, for each of the source/detector geometries, an effective absorption coefficient and an effective reduced scattering coefficient of the volume of interest;
   detecting at the detector locations the fluorescence wavelength and generating a fluorescence signal output;
   calculating a fluorescence signal using an estimated spatial distribution of fluorophore concentration and the effective absorption and reduced scattering coefficients for each of the source/detector geometries; and
   adjusting said estimated spatial distribution of fluorophore concentration using said detected fluorescence signal output and said calculated fluorescence signal to generate said image.

2. A method according to claim 1 wherein determining an effective absorption coefficient and an effective reduced scattering coefficient comprises time-resolved detecting the excitation wavelength and determining said coefficients from the detected signal.

3. A method according to claim 2 wherein optically scanning the volume of interest comprises optically scanning the volume of interest with a pulsed laser source, detecting the excitation wavelength comprises detecting the excitation wavelength with a time domain detector, and determining said absorption and reduced scattering coefficients for each source/detector geometry comprises compiling a temporal point spread function.

4. A method according to claim 1 wherein determining an effective absorption coefficient and an effective reduced scattering coefficient comprises determining said coefficient values for each source-detector geometry from a dataset containing a spatial distribution of absorption and reduced scattering coefficients in said volume of interest.

5. A method according to claim 4, wherein said dataset containing a spatial distribution of absorption and reduced scattering coefficients is obtained by optical imaging of said volume of interest.

6. A method according to claim 4, wherein said dataset containing a spatial distribution of absorption and reduced scattering coefficients is obtained by determining an anatomical geometry of said volume of interest, and morphing according to said anatomical geometry a generic dataset containing a spatial distribution of absorption and reduced scattering coefficients.

7. A method according to claim 1 wherein optically scanning the volume of interest comprises optically scanning the volume of interest with a continuous wave optical source, and wherein detecting the fluorescence wavelength comprises detecting the fluorescence wavelength with a continuous wave detector.

8. A method according to claim 1 wherein optically scanning the volume of interest comprises optically scanning the volume of interest with a continuous wave optical source and a pulsed optical source, wherein detecting the fluorescence wavelength comprises detecting the fluorescence wavelength with a continuous wave detector and a time resolved detector.

9. A method according to claim 6 wherein calculating a fluorescence signal comprises calculating a fluorescence signal using a continuous wave photon migration model calculator and a time domain photon migration model calculator.

10. A method according to claim 1 further comprising repeating the steps of calculating a fluorescence signal and adjusting said estimated spatial distribution so as to reduce differences between the calculated fluorescence signal and the detected fluorescence signal output.

11. A method according to claim 1 further comprising normalizing the fluorescence signal output.

12. A fluorescence optical tomography method for producing an image of a volume of interest indicative of location and number density of fluorophores embedded therein, the method comprising:
optically scanning the volume of interest at a plurality of source/detector geometries with an optical source generating an optical signal at an excitation wavelength, interaction of the excitation wavelength with the fluorophores causing fluorescence therefrom at a fluorescence wavelength;
detecting the excitation wavelength with a time domain detector and compiling a temporal point spread function, and determining separately, for each of the source/detector geometries, an absorption coefficient and a reduced scattering coefficient;
calculating a fluorescence signal using an estimated spatial distribution of fluorophore concentration and the effective absorption and reduced scattering coefficients for each of the source/detector geometries;
detecting the fluorescence wavelength and generating a fluorescence signal output; and
estimating values of fluorophore concentration as a function of position within the volume of interest using the fluorescence signal output and the calculated fluorescence signal to generate said image.

13. A fluorescence optical tomography system for producing an image of a volume of interest indicative of location and number density of fluorophores embedded therein, the system comprising:
at least one optical source and at least one optical detector which together allow for optical scanning of the volume of interest at a plurality of source/detector geometries, the optical source generating an optical signal at an excitation wavelength such that interaction of the excitation wavelength with the fluorophores causes fluorescence therefrom at a fluorescence wavelength;
a determinator which determines separately, for each of the source/detector geometries, an absorption coefficient and a reduced scattering coefficient;
a calculator which calculates a fluorescence signal using an estimated spatial distribution of fluorophore concentration and the effective absorption and reduced scattering coefficients for each of the source/detector geometries;
a fluorescence signal generator which, using detected fluorescence wavelengths, generates a fluorescence signal output; and
an estimator which adjusts the estimated spatial distribution of fluorophore concentration from said fluorescence signal output and said calculated fluorescence signal to generate image data.

14. A system according to claim 13 wherein the determinator determines the absorption coefficient and the reduced scattering coefficient using time resolved detection of the excitation wavelength.

15. A system according to claim 14 wherein the optical source comprises a pulsed laser source and the detector comprises a time domain detector, and wherein the system further comprises a compiler for compiling a temporal point spread function from a signal detected by the time domain detector and providing the temporal point spread function to the determinator.

16. A system according to claim 13 wherein the determinator, in determining an absorption coefficient and a reduced scattering coefficient calculates an effective absorption coefficient and an effective reduced scattering coefficient from a dataset containing a spatial distribution of absorption and reduced scattering coefficients in said volume of interest.

17. A system according to claim 16 wherein said dataset is obtained by optical imaging of said volume of interest.

18. A system according to claim 16 wherein said dataset is obtained by determining an anatomical geometry of said volume of interest and morphing according to said anatomical geometry a generic dataset containing a spatial distribution of absorption and reduced scattering coefficients.

19. A system according to claim 13 wherein the optical source comprises a continuous wave optical source, and wherein the detector comprises a continuous wave detector that detects the fluorescence wavelength.

20. A system according to claim 13 wherein the optical source comprises a continuous wave optical source and a pulsed optical source, and wherein the detector comprises a continuous wave detector and a time resolved detector both of which detect the fluorescence wavelength.

21. A system according to claim 13 wherein the calculator calculates the fluorescence signal using a continuous wave photon migration model calculator and a time domain photon migration model calculator.

22. A system according to claim 13 wherein the calculator uses the adjusted estimated spatial distribution of fluorophore concentration to recalculate the fluorescence signal, and wherein the estimator readjusts the estimated spatial distribution of fluorophore concentration using the recalculated fluorescence signal and said fluorescence signal output.

23. A system according to claim 13 further comprising a normalizer that normalizes the fluorescence signal output.

* * * * *